United States Patent [19]

Moore et al.

[11] Patent Number: 4,996,229
[45] Date of Patent: Feb. 26, 1991

[54] SCYTOPHYCINS

[75] Inventors: Richard E. Moore; Eiichi Furusawa; Ted R. Norton; Gregory M. L. Patterson, all of Honolulu, Hi.; Jon S. Mynderse, Indianapolis, Ind.

[73] Assignees: University of Hawaii, Honolulu, Hi.; Eli Lilly and Company, Indianapolis, Ind.

[21] Appl. No.: 401,353

[22] Filed: Aug. 31, 1989

Related U.S. Application Data

[60] Division of Ser. No. 865,499, May 21, 1986, Pat. No. 4,863,955, which is a continuation-in-part of Ser. No. 741,776, Jun. 6, 1985, abandoned, which is a continuation-in-part of Ser. No. 741,778, Jun. 6, 1985, abandoned.

[51] Int. Cl.$^5$ .................. A61K 31/365; C07D 303/12; C07D 313/08
[52] U.S. Cl. .................... 514/450; 549/265; 549/267; 549/270; 549/271
[58] Field of Search ................ 514/450; 549/265, 267, 549/271, 270

[56] References Cited

U.S. PATENT DOCUMENTS 4,342,751  8/1982  Moore et al. ..................... 424/177

OTHER PUBLICATIONS

R. E. Moore in Marine Natural Products: Chemical and Biological Perspectives, P. J. Scheuer, ed., vol. IV, pp. 1-52, Academic Press, New York (1981).
M. Kashiwagi et al., "Antineoplastic Evaluation of Pacific Basin Marine Algae," J. Pharm. Sciences 69 (6), 735-738 (1980).
S. Carmely et al., "Structure of Swinholide-A, A New Macrolide from the Marine Sponge Theonella Swinhoei", Tetrahedron Letters, 1985, 511-514.
R. E. Moore, "Toxins from Blue-Green Algae", *Bioscience 27 (12), 797-802.*
R. E. Moore et al., "Toxins from Cyanophytes Belonging to the Scytonemataceae," *Pure & Appl. Chem.* 58 (2), 263-271 (1986).
J. A. Roesener et al., "Ulapualide A and B, Extraordinary Antitumor Macrolide from Nudibranch Eggmasses," *J. Am. Chem. Soc.,* 1986, 108, 846-847.
S. Matsunaga et al., "Kabiramide C, a Novel Antifungal Macrolide from Nudibranch Eggmasses," *J. Am. Chem. Soc.,* 1986, 108, 847-849.
*Chemical Abstracts* (1987), 106:153049e, Moore et al., "Scytophycins, Potent Cytotoxic Macrolides from Blue-Green Alga."
M. Ishibashi et al., *J. Org. Chem. (1986), 51, 5300-5306, "Scytophycins, Cytotoxic and Antimicotic Agents from the Cyanophyte Scytonema pseudohofmanni."*

*Primary Examiner*—Richard L. Raymond
*Assistant Examiner*—Mark W. Russell
*Attorney, Agent, or Firm*—Nancy J. Harrison; Leroy Whitaker

[57] ABSTRACT

Scytophycins A, B, C, D and E, an aldehyde and alcohol derivative of scytophycin B and the specified alkanoyl and benzoyl esters of scytophycins A, B, C, D and E and the B derivatives (scytophycin compounds) are novel antineoplastic and antifungal agents. Antifungal compositions containing a scytophycin compound and methods of inhibiting fungi, especially plant pathogenic fungi, using these compositions are included. A method for producing the scytophycin complex, comprising scytophycins A, B, C, D and E, using a new strain of the blue-green alga *Scytonema pseudohofmanni,* and a biologically purified culture of the alga are also provided.

5 Claims, 3 Drawing Sheets

SCYTOPHYCINS

This invention was supported in part by a grant (PHS grant CA12623) of the National Cancer Institute, Department of Health and Human Services.

Cross Reference to Related Applications

This application is a division of application Ser. No. 06/865,499 filed May 21, 1986, now U.S. Pat. No. 4,863,955 which in turn is a continuation-in-part of application Ser. No. 06/741,776 filed June 6, 1985, now abandoned, which is a continuation-in-part of application Ser. No. 06/741,778 filed June 6, 1985, now abandoned.

SUMMARY OF THE INVENTION

This invention relates to five new pharmacologically-active compounds, scytophycins A, B, C, D and E, which have been isolated from the blue-green alga *Scytonema pseudohofmanni*, to an aldehyde and alcohol derivative of scytophycin B and to certain acyl esters of these compounds. In other aspects, this invention relates to a method for producing scytophycins A, B, C, D and E by culturing a new strain of Scytonema pseudohofmanni, Bharadwaja ATCC 53141, and to a biologically purified culture of the novel *S. pseudohofmanni* strain.

This invention further relates to a method for using scytophycins A, B, C, D and E and specified acyl esters of these compounds to inhibit fungi, in particular, fungal plant pathogens. Fungicidal compositions containing scytophycins A, B, C, D and E and their specified esters are also part of this invention.

DETAILED DESCRIPTION OF THE INVENTION

Neoplastic diseases (cancer) continue to be a widespread problem. Although the mechanisms by which such diseases invade the body have been under intensive investigation for a number of years, much remains to be learned before this problem can be solved. Thus, novel antineoplastic agents are quite useful because they contribute to a general understanding of the underlying mechanisms by which malignant cells proliferate.

Fungal plant pathogens cause great economic losses each year. New agents effective against these phytopathogens are needed. Presently used fungicides differ in their effectiveness against specific fungi. In addition, resistant fungal strains frequently develop, creating a continual need for new, effective agents. Furthermore, some fungicides are difficult to obtain and, thus, expensive to use. Fungicides which are less expensive are, therefore, quite beneficial.

This invention relates to a compound selected from scytophycins A, B, C, D and E, an aldehyde and primary alcohol derivative of B, and the $C_1$–$C_6$-alkanoyl and benzoyl and the halo-, hydroxy- and $C_1$–$C_3$-alkoxy-substituted $C_1$–$C_6$-alkanoyl and benzoyl esters of scytophycins A, B, C, D and E and the specified B derivatives. For convenience, these compounds will be called scytophycin compounds.

The scytophycin compounds are potent cytotoxins and antineoplastic agents. In addition, they inhibit fungal pathogens. For example, scytophycins A and B inhibit *Candida albicans*, the causative agent for candidiasis in animals and man. The scytophycin compounds also inhibit fungal plant pathogens such as *Pythium ultimum* (Phycomycetes), which causes damping-off diseases of seedlings, *Rhizoctonia solani* (Basidiomycetes), which causes damping-off and stem rot and *Sclerotinia homoeocarpa* (ascomycetes), which causes diseases of turf grasses.

Thus, this invention further relates to a method for treating pathogenic fungi which comprises contacting the loci of the fungi with a fungicidally-effective amount of a scytophycin compound.

The scytophycin complex, comprising major factors A, B and C and minor factors D and E, was isolated from a strain of an epidaphic variety of the blue-green alga *Scytonema pseudohofmanni Bharadwaja (Scytonemataceae)*. The new strain is a clonal culture isolated after repeated subculture of an algal sample collected in a moist, heavily forested region of the Koolauloa District on the island of Oahu, Hi.

The *Scytonema pseudohofmanni* culture of this invention has been deposited and made part of the stock culture collection of the American Type Culture Collection, 12301 Parklawn Drive, Rockville, Md. 20852, from which it is available to the public under the accession number ATCC 53141.

As is the case with other organisms, the characteristics of *Scytonema pseudohofmanni* ATCC 53141 are subject to variation. For example, recombinants, variants or mutants of the ATCC 53141 strain may be obtained by treatment with various known physical and chemical mutagens, such as ultraviolet rays, X rays, gamma rays, and N-methyl-N'-nitro-N-nitrosoguanidine. All natural and induced variants, mutants and recombinants of *Scytonema pseudohofmanni* ATCC 53141 which retain the characteristic of producing scytophycin A, B, C, D or E may be used in this invention.

Scytophycin B, which is the major metabolite produced by the new *Scytonema pseudohofmanni* strain, is believed to have the structure shown in formula 1.

Scytophycin B has the following characteristics:
  Form: white amorphous solid
  Empirical formula: $C_{45}H_{73}NO_{12}$
  Molecular weight: 819 [determined by fast-atom bombardment mass spectrometry (FABMS)]
  UV $\lambda_{max}$ (ethanol): 264 nm ($\epsilon$ 28,500)
  $[\alpha]_D^{20}$: $-24°$ (c 0.63, MeOH)
  CD (MeOH): $[\theta]_{266}$ +16,000
  IR ($CHCl_3$) 1690, 1660 and 1125 $cm^{-1}$
  $^1$H NMR: (Table 1)
  $^{13}$C NMR: (Table 3)
  MS (FAB): m/z 858 $(M+K)^+$, 842 $(M+Na)^+$ and 820
  $(M+H)^+$; Found m/z 802.5123. Calcd for $C_{45}H_{72}NO_{11}$:
  $(M-H_2O+H)$ 802.5105.

Scytophycin A, which is a second metabolite produced by the *S. pseudohofmanni* culture, is believed to have the structure shown in formula 2.

Scytophycin A has the following characteristics:
  Empirical formula: $C_{45}H_{75}NO_{12}$
  Molecular weight: 821 (determined by FABMS)
  UV $\lambda_{max}$ (ethanol): 264 nm ($\epsilon$ 35,000)
  Form: white amorphous solid
  $[\alpha]_D^{22}$: $-35°$ (c 1.3, MeOH)
  CD (MeOH): $[\theta]_{266}$ +12,200
  IR ($CHCl_3$): 1690, 1660 and 1120 $cm^{-1}$
  $^1$H NMR: (Table 1)
  $^{13}$C NMR: (Table 3)
  MS(FAB): m/z 860 $(M+K)^+$, 844 $(M+Na)^+$ and 822
  $(M+H)^+$; Found m/z 822.5407. Calcd for $C_{45}H_{76}NO_{12}$;
  $(M+H)$ 822.5368.

Figure 1:
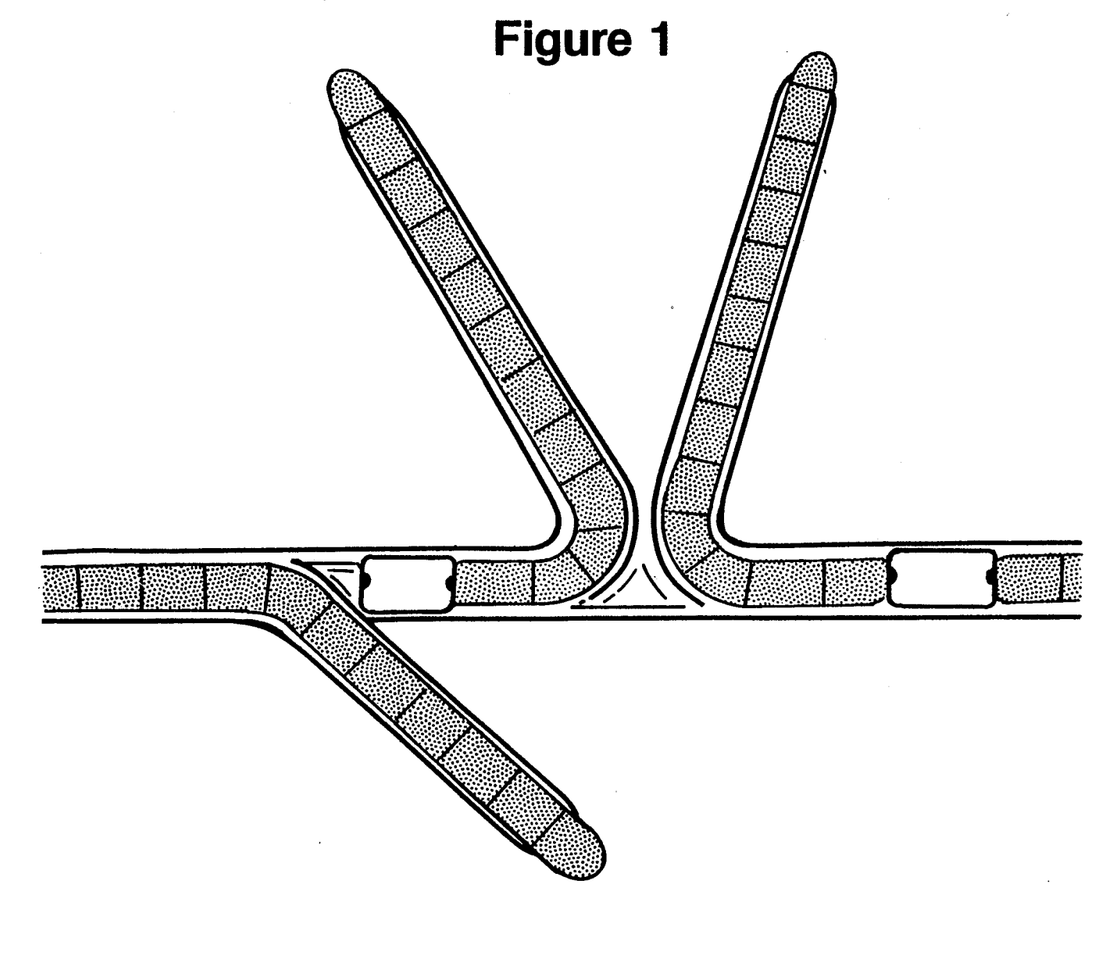
FIG. 1 shows the mature filaments of the new strain of *Scytonema pseudohofmanni* Bharadwaja (Nostocales, Scytonemataceae). As shown, the filaments have single and geminate false branches and single intercalary heterocysts somewhat broader than the trichome. The scale bar represents 20 $\mu$m.
Figure 2:
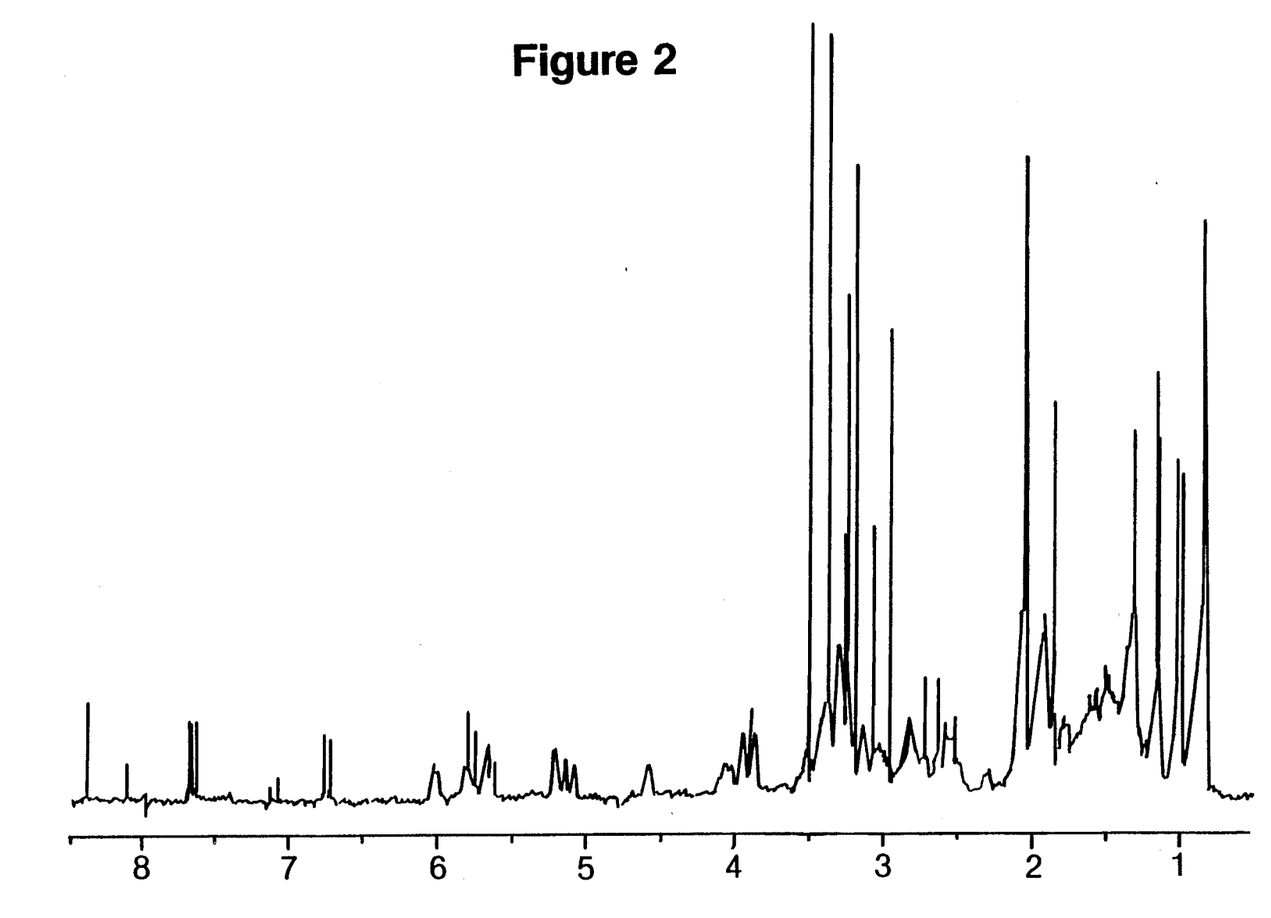
FIG. 2 shows the 360 MHz proton nuclear magnetic resonance ($^1$H NMR) spectrum of scytophycin A in acetone $d_6$.
Figure 3:
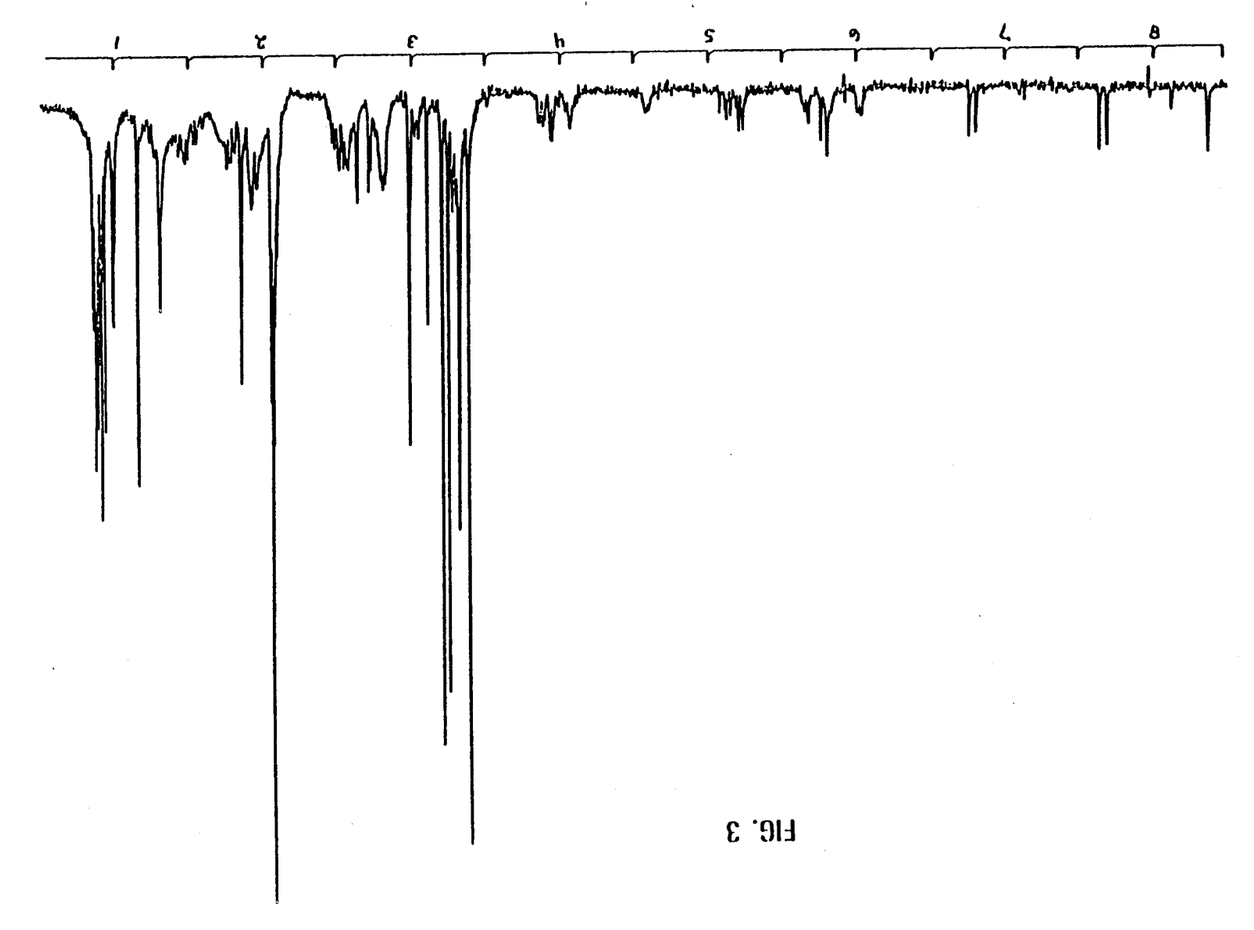
FIG. 3 shows the 360 MHz $^1$H NMR spectrum of scytophycin B in acetone $d_6$.

Table 1 summarizes and compares the $^1$H NMR spectral data for scytophycins A and B. The spectra are shown in FIGS. 2 and 3.

TABLE 1

The $^1$H NMR Data in Acetone $d_6$ for Scytophycins A and B.

| Assignment | Scytophycin B | Scytophycin A |
|---|---|---|
| 1 | — | — |
| 2 | 5.78 | 5.78 |
| 3 | 7.66 | 7.65 |
| 4 | — | — |
| 4-Me | 1.85 | 1.80 |
| 5 | 6.02 | 6.01 |
| 6 | 2.48 | 2.43 |
|   | 2.57 | 2.57 |
| 7 | 4.06 | 4.06 |
| 8 | 1.26 | ~1.2 |
|   | 1.77 | 1.71 |
| 9 | 4.58 | 4.57 |
| 10 | 5.66 | 5.66 |
| 11 | 5.81 | 5.81 |
| 12 | 1.91 | 1.91 |
| 13 | 3.39 | 3.38 |
| 14 | 1.46 | 1.46 |
|   | 1.55 | 1.54 |
| 15 | 3.94 | 3.93 |
| 15-OMe | 3.37 | 3.37 |
| 16 | — | — |
| $CH_2$-16 | 2.63 | 2.63 |
|   | 2.72 | 2.72 |
| 17 | 3.88 | 3.84 |
| 17-OMe | 3.24 | 3.24 |
| 18 | 1.46 | 1.43 |
|   | 1.96 | 1.94 |
| 19 | 3.31 | 3.30 |
| 19-OMe | 3.20 | 3.19 |
| 20 | 2.09 | 2.09 |
| 20-Me | 0.86 | 0.84 |
| 21 | 5.22 | 5.20 |
| 22 | 1.99 | 1.93 |
| 22-Me | 0.88 | 0.84 |
| 23 | 3.03 | 3.02 |
| 24 | 1.69 | 1.68 |
| 24-Me | 0.99 | 1.00 |
| 25 | 1.37 | NA* |
|   | 1.75 | NA |
| 26 | 2.54 | 2.29 |
|   |   | 1.55 |
| 27 | — | 3.39 |
| 28 | 2.78 | 1.58 |

TABLE 1-continued

The $^1$H NMR Data in Acetone $d_6$ for Scytophycins A and B.

| Assignment | Scytophycin B | Scytophycin A |
|---|---|---|
| | (2.74)** | |
| 28-Me | 0.92 | 0.84 |
| 29 | 3.28 | 3.12 |
| 29-OMe | 3.31 | 3.12 |
| 30 | 2.46 | 2.51 |
| 30-Me | 1.15 | 1.13 |
| 31 | 5.12 | 5.11 |
| | (5.18) | (5.19) |
| 32 | 6.79 | 6.74 |
| | (7.11) | (7.09) |
| 33-NMe | 2.99 | 2.96 |
| | (3.11) | (3.07) |
| 34 | 8.36 | 8.35 |
| | (8.11) | (8.09) |

*NA = not assigned
**( )indicates chemical shift of protons in minor conformer due to restricted rotation around C(32)-N(33) and N(33)-C(34) bonds Scytophycin C, a third metabolite produced by the S. pseudohofmanni culture, is believed to have the structure shown in formula 3

CD (MeOH): $[\theta]_{265}$ +10,600
UV $\lambda_{max}$ (MeOH): 262 nm ($\epsilon$ 48,000)
IR (CHCl$_3$) 1690, 1660 and 1115 cm$^{-1}$
$^1$H NMR: (Table 2)
$^{13}$C NMR: (Table 3)
MS (FAB): m/z 828 (M+Na)$^+$, 788 (M—H$_2$O+H)$^+$ and 156 (CH$_3$O$^+$=CH—CH(CH$_3$)—CH=CH—N(CH$_3$)—CHO).

Scytophycin D, which is a minor metabolite produced by the S. pseudohofmanni culture, is believed to have the structure shown in formula 4.

4

Scytophycin D has the following characteristics:
Form: white amorphous solid
Empirical Formula: C$_{45}$H$_{75}$NO$_{12}$
Molecular Weight: 821
$[\alpha]_D^{20}$: $-32°$ (c 0.90, MeOH)
CD (MeOH): $[\theta]_{265}$ +13,400
UV $\lambda_{max}$ (MeOH): 265 nm ($\beta$ 47,000)
IR (CHCl$_3$): 1690, 1660 and 1120 cm$^{-1}$
$^1$H NMR: (Table 2)
$^{13}$C NMR: (Table 3)
MS (FAB): m/z 844 (M+Na)$^+$, 804

3

Scytophycin C has the following characteristics:
Form: white amorphous solid
Empirical Formula: C$_{45}$H$_{75}$NO$_{11}$
Molecular Weight: 805
$[\alpha]_D^{18}$: $-23°$ (c 1.2, MeOH)

(M—H$_2$O+H)$^+$ and
156 (CH$_3$O$^+$=CH—CH(CH$_3$)—CH=CH—N(CH$_3$)—CHO).

Scytophycin E, which is another minor metabolite produced by the S. pseudohofmanni culture, is believed to have the structure shown in formula 5.

Scytophycin E has the following characteristics:
Form: white amorphous solid
Empirical Formula: $C_{45}H_{75}NO_{12}$
Molecular Weight: 821

$[\alpha]_D^{19}$: $-38°$ (c 1.0, MeOH)
CD (MeOH): $[\theta]_{26}$ +27,000
UV $\lambda_{max}$ (MeOH): 265 nm ($\epsilon$ 39,000)
IR (CHCl$_3$): 1690, 1660 and 1090 cm$^{-1}$
$^1$H NMR: (Table 2)
$^{13}$C NMR: (Table 3)
MS (FAB): m/z 844 (M+Na)$^+$, 804 (M—H$_2$O+H)$^+$ and
156 (CH$_3$O$^+$=CH—CH(CH$_3$)—CH=CH—N(CH$_3$)—CHO);

Found: m/z 844.5190. Calcd for $C_{45}H_{75}NO_{12}Na$: (M+Na)$^+$ 844.5187.

The scytophycin factors thus appear to have the common structure shown in formula 6.

| No. | Compound |
|---|---|
| 1 | Scytophycin B: R$^1$ and R$^2$ = —O—; R$^3$ and R$^4$ = =O |
| 2 | Scytophycin A: R$^1$ and R$^2$ = —O—; R$^3$ = H; R$^4$ = OH |
| 3 | Scytophycin C: R$^1$ = R$^2$ = H; R$^3$ and R$^4$ = =O |
| 4 | Scytophycin D: R$^1$ = OH; R$^2$ = H; R$^3$ and R$^4$ = =O |
| 5 | Scytophycin E: R$^1$ = H; R$^2$ = OH; R$^3$ and R$^4$ = =O |

Table 2 summarizes and compares the $^1$H NMR spectral data for scytophycins C, D and E.

TABLE 2

| | $^1$H NMR Data for Scytophycins C, D and E in Acetone-d$_6$ ($\delta$) | | |
|---|---|---|---|
| | Scytophycin | | |
| Assignment | C | D | E |
| 2 | 5.78 d (15.8) | 5.76 d (15.6) | 5.75 d (15.6) |
| 3 | 7.61 d (15.8) | 7.47 d (15.6) | 7.64 d (15.6) |
| Me on 4 | 1.82 br s | 1.84 br s | 1.82 br s |
| 5 | 6.03 br d (9, 4.5) | 5.87 br t (8) | 6.01 br d (8.7, 3.9) |
| 6 | 2.46 | 2.50 | 2.52 |
| 6' | 2.46 | | |
| 7 | 4.02 t | 4.01 br s | 4.03 br t |
| 8 | 1.28 | 1.22 | 1.34 |
| 8' | 1.77 | 1.73 | 1.78 |
| 9 | 4.53 br d (9) | 4.47 br d (10.5) | 4.57 br d (7.5) |
| 10 | 5.67 br d (10) | 5.63 br d (10) | 5.66 br d (10.5) |
| 11 | 5.77 m | 5.76 m | 5.78 m |
| 12 | 1.89 | 2.05 | 1.95 |
| 12' | * | * | * |
| 13 | 3.34 | 3.27 | 3.28 |
| 14 | 1.68 | 1.85 | 1.86 |
| 14' | 1.63 | 1.60 | 1.79 |
| 15 | 3.62 br d | 3.58 br s | 3.80 |
| MeO on 15 | 3.30 s | 3.38 s | 3.36 s |
| 16 | 1.68 | — | 1.67 |
| Me on 16 | 0.80 d (6.9) | 1.00 s | — |
| CH$_2$ on 16 | — | — | 3.80 br d (9) |

TABLE 2-continued

¹H NMR Data for Scytophycins C, D and E in Acetone-d₆ (δ)

| Assignment | Scytophycin C | D | E |
|---|---|---|---|
| 17 | 3.49 dd | 3.52 dd | 3.65 m |
|  |  |  | 3.47 t |
| MeO on 17 | 3.23 s | 3.24 s | 3.18 s |
| 18 | 1.78 | 1.97 | 1.97 |
| 19 | 3.47 | 3.45 | 3.74 |
| MeO on 19 | 3.17 s | 3.39 s | 3.19 s |
| 20 | 2.04 | 2.16 | 2.10 |
| Me on 20 | 0.89 d (7.1) | 0.87 d (7.6) | 0.90 d (6.9) |
| 21 | 5.16 br d(10.5) | 5.27 br d (10) | 5.18 br d (9.6) |
| 22 | 2.00 | 1.96 | 2.03 |
| Me on 22 | 0.84 d (6.9) | 0.84 d (6.6) | 0.85 d (6.9) |
| 23 | 3.00 | 3.01 | 3.13 |
| OH on 23 | * | 3.88 d (4.5) | 4.12 d (4.5) |
| 24 | 1.67 | 1.66 | 1.74 |
| Me on 24 | 0.97 d (6.7) | 0.95 d (6.7) | 0.97 d (6.6) |
| 25 | 1.38 | 1.42 | 1.35 |
| 25' | 1.76 | 1.74 | 1.71 |
| 26 | 2.55 | 2.53 | 2.54 |
| 26' | 2.55 | 2.53 | 2.54 |
| 28 | 2.77 | 2.76 | 2.76 |
| Me on 28 | 0.90 d (7.0) | 0.90 d (7.1) | 0.90 d (6.9) |
| 29 | 3.27 | 3.30 | 3.28 |
| MeO on 29 | 3.29 s | 3.29 s | 3.30 s |
| 30 | 2.44 | 2.41 | 2.47 |
| Me on 30 | 1.13 d (7.0) | 1.13 d (6.9) | 1.13 d (6.9) |
| 31 | 5.12 dd (14.2, 9.3) | 5.10 dd (14.1, 9) | 5.10 dd (14.1, 9) |
| 31** | 5.17 dd (14.7, 9) | 5.16 dd (14.7, 9) | 5.17 dd (14.7, 9) |
| 32 | 6.77 d (14.2) | 6.77 d (14.1) | 6.77 d (14.1) |
| 32** | 7.09 d (14.7) | 7.09 d (14.7) | 7.09 d (14.7) |
| Me on N-33 | 2.97 s | 2.97 s | 2.97 s |
| Me on N-33** | 3.09 s | 3.09 s | 3.09 s |
| 34 | 8.34 s | 8.34 s | 8.34 s |
| 34** | 8.09 s | 8.10 s | 8.10 s |

*not assigned
**signals of the minor conformer

Table 3 summarizes the ¹³C NMR chemical shift data for scytophycins A, B, C, D and E.

TABLE 3

¹³C NMR Data for Scytophycins A, B, C, D and E in Acetone-d₆

| Assignment[a] | Scytophycin A | B[b] | C | D | E |
|---|---|---|---|---|---|
| 1 | 169.57 | 169.63 | 169.38 | 168.83 | 169.61 |
| 2 | 115.63 | 115.58 | 115.71 | 116.38 | 115.68 |
| 3 | 151.81 | 151.85 | 151.33 | 151.12 | 151.70 |
| 4 | 134.77 | 134.76 | 134.69 | 135.03 | 134.76 |
| Me on 4 | 12.30 | 12.29 | 12.09 | 12.27 | 12.24 |
| 5 | 139.90 | 139.95 | 139.73 | 139.55 | 139.93 |
| 6 | 41.54 | 42.08 | 41.92 | 42.10 | 42.11 |
| 7 | 68.91 | 68.86 | 68.54 | 68.02 | 68.82 |
| 8 | 41.06 | 41.51 | 41.19 | 40.48 | 41.61 |
| 9 | 70.79 | 70.91 | 70.76 | 70.39 | 70.98 |
| 10 | 131.52 | 131.51 | 131.48 | 131.32 | 131.67 |
| 11 | 125.02 | 124.90 | 124.48 | 124.85 | 124.76 |
| 12 | 31.85 | 31.84 | 32.19 | 31.18 | 31.48 |
| 13 | 66.86 | 66.87 | 65.75 | 65.94 | 66.04 |
| 14 | 34.76 | 35.63 | 32.61 | 32.50 | 32.21 |
| 15 | 78.42 | 78.44 | 79.79 | 78.46 | 79.94 |
| MeO on 15 | 57.46 | 57.46 | 56.46 | 57.19 | 57.12 |
| 16 | 61.69 | 61.12 | 40.93 | 82.73 | 46.95 |
| CH₂(3)-16 | 45.66 | 45.56 | 9.25 | 18.08 | 59.58 |
| 17 | 75.27 | 75.20 | 76.32 | 76.25 | 76.70 |
| MeO on 17 | 52.89 | 52.83 | 53.55 | 58.25 | 51.87 |
| 18 | 27.49 | 27.45 | 27.31 | 27.92 | 27.18 |
| 19 | 77.47 | 77.49 | 77.93 | 77.35 | 77.44 |
| MeO on 19 | 57.78 | 57.78 | 58.03 | 58.25 | 58.12 |
| 20 | 38.14 | 38.15 | 40.29 | 40.36 | 40.02 |
| Me on 20 | 9.36 | 9.23 | 9.05 | 9.23 | 9.37 |
| 21 | 76.51 | 76.51 | 76.56 | 76.52 | 76.52 |
| 22 | 37.90 | 38.15 | 38.45 | 38.19 | 38.80 |
| Me on 22 | 9.27 | 9.23 | 8.79 | 9.23 | 9.27 |
| 23 | 76.51 | 76.51 | 77.18 | 76.44 | 76.30 |
| 24 | 34.29 | 33.78 | 33.69 | 33.87 | 33.85 |
| Me on 24 | 18.63 | 18.27 | 18.13 | 18.25 | 18.31 |
| 25 | 25.74 | 22.71 | 22.55 | 22.74 | 22.71 |
| 26 | 39.39 | 39.36 | 39.17 | 39.48 | 39.43 |
| 27 | 71.00 | 214.07 | 213.84 | 213.98 | 213.93 |
| 28 | 35.72 | 49.48 | 49.33 | 49.50 | 49.50 |
| Me on 28 | 9.84 | 13.65 | 13.47 | 13.65 | 13.64 |
| 29 | 88.66 | 88.26 | 88.11 | 88.28 | 88.27 |
| MeO on 29 | 61.13 | 61.12 | 60.96 | 61.13 | 61.14 |
| 30 | 38.53 | 37.98 | 38.03 | 36.83 | 38.21 |
| 30[c] | 38.71 | 38.35 | 38.18 | 38.36 | 38.36 |
| Me on 30 | 20.06 | 19.45 | 19.45 | 19.62 | 19.63 |
| 31[c] | 112.27 | 111.18 | 110.97 | 111.10 | 111.09 |
| 31[c] | 114.20 | 113.25 | 113.05 | 113.18 | 113.16 |
| 32 | 129.65 | 130.15 | 129.98 | 130.17 | 130.17 |
| 32[c] | 124.76 | 125.44 | 125.46 | 125.46 | 125.45 |
| Me on N-33 | 27.22 | 27.22 | 27.03 | 27.19 | 27.18 |
| Me on N-33[c] | 33.02 | 33.03 | 32.85 | 33.00 | 33.01 |
| 34 | 162.81 | 162.89 | 162.71 | 162.83 | 162.84 |
| 34[c] | 161.52 | 161.60 | 161.62 | 161.58 | 161.58 |

[a] 75 MHz; acetone-d₆ as internal reference = 29.80 ppm.
[b] ¹H-¹³C connectivities determined using a phase-cycled 16-step heteronuclear chemical shift correlation map experiment.
[c] Signals for the minor conformer.

Scytophycin B has been converted to two useful derivatives. When scytophycin B was treated with acetic acid and ethanol at room temperature for a day, the aldehyde of formula 7 was formed. This aldehyde was reduced with sodium borohydride to give the primary alcohol of formula 8.

7: $R^3$ = CHO
8: $R^3$ = $CH_2OH$

The $^1$H NMR spectra of compounds 7 and 8 are summarizes in Table 4.

TABLE 4

$^1$H NMR Spectra of Compounds 7 and 8 in Acetone-$d_6$ (δ)

| Position[a] | 7 | 8 |
|---|---|---|
| 2 | 5.71 | 5.70 |
| 3 | 7.43 | 7.42 |
| Me on 4 | 1.79 | 1.80 |
| 5 | 5.86 | 5.88 |
| 6 | 2.42 | |
| 6' | 2.51 | |
| 7 | 3.96 | 3.97 |
| 8 | 1.25 | |
| 8' | 1.78 | |
| 9 | 4.51 | 4.50 |
| 10 | 5.62 | 5.64 |
| 11 | 5.76 | 5.77 |
| 12 | 1.88 | |
| 13 | 3.40 | |
| 14 | 1.44 | |
| 14' | 1.55 | |
| 15 | 3.84 dd | 3.81 |
| $CH_2$ on 16 | 2.65 d | |
|  | 2.55 d | |
| 17 | 3.77 dd | |
| 18 | 1.44 | |
| 18' | 1.90 | |
| 19 | 3.23 | |
| 20 | 1.98 | |
| Me on 20 | 0.85 | 0.89 |
| 21 | 5.20 | 5.20 |
| 22 | 2.13 | |
| Me on 22 | 0.77 | 0.78 |
| 23 | 3.08 | |
| 24 | 2.13 | |
| Me on 24 | 1.06 | 1.06 |
| 25 ax | 1.12[b] | |
| 25 eq | 1.25[b] | |
| 26 ax | 0.90[b] | |
| 25 eq | 1.77[b] | |
| 28 | 1.73 | |
| Me on 28 | 0.87 | 1.04 |
| 29 | 3.37 | |
| 30 | 2.31 | |
| Me on 30 | 0.92 | 0.91 |
| 31 | 2.58 | |
| 32 | 9.81 | 3.64 |
| 32' | | 3.54 |
| OMe | 3.36 | 3.38 |
| OMe | 3.31 | 3.27 |
| OMe | 3.19 | 3.19 |
| OMe | 3.19 | 3.19 |

[a]300 MHz; residual acetone-$d_5$ as internal reference = 2.04 ppm.
[b]Tentative assignments.

As will be apparent from their structures, scytophycins A, B, C, D and E and the derivatives of B have hydroxyl groups which are capable of esterification. In addition, the primary alcohol of Compound 8 can be acylated. In scytophycin B, the hydroxyl group at C-7 is acylated more readily than that at C-23. The $C_1$–$C_6$-alkanoyl and benzoyl esters or the halo-, hydroxy-or $C_1$–$C_3$-alkoxy-substituted $C_1$–$C_6$ alkanoyl or benzoyl esters of the scytophycin factors and of compounds 7 and 8 are also part of this invention.

At sublethal doses, the scytophycin compounds are antineoplastic agents. The minimum lethal dose of scytophycin B in mice, when administered IP, is about 650 μg/kg. Its toxicity is comparable to that of curare and strychnine, but is almost two orders of magnitude less than that of saxitoxin and tetrodotoxin.

The scytophycin compounds are potent cytotoxins. For example, the minimum toxic doses of scytophycins A and B against KB human epidermoid carcinoma and NIH/3T3 mouse fibroblast cell lines were determined to be 1 ng/mL and 0.65 ng/mL, respectively, using methods described by E. Furusawa and W. Cutting in Ann. New York Acad. Sci. 173, 669–679 (1970).

Both scytophycin A and scytophycin B exhibited moderate activity against intraperitoneally implanted P388 lymphocytic leukemia and Lewis lung carcinoma, but did not exhibit activity against intraperitoneally implanted B16 melanoma.

Female hybrid BDF1 (DBA/2×C57BL/6) mice were used for the evaluation of the scytophycins against the three tumors. The mice were first inoculated intraperitoneally with $10^6$ cells of P388 ascites leukemia (P388), 2 to 6×$10^5$ cells of Lewis lung carcinoma (LLC) homogenate, or 0.3 mL of 20% homogenate of B16 tumor (B16) masses. Drug treatment was started the next day (Day 1) and continued daily for 6–9 days. The results of these tests are summarized in Table 5.

TABLE 5
Effect of the Scytophycins on Intraperitoneally Implanted P388 Lymphocytic Leukemia, Lewis Lung Carcinoma, and B16 Melanoma in BDF1 Mice

| Scyto-phycin | Tumor | Dose μg/Mouse | Days of Treatment | Mean Survival Time, Days Treated | Mean Survival Time, Days Controls | % T/C[a] |
|---|---|---|---|---|---|---|
| A | P388 | 1 | 8 | 10.0 | 8.0 | 125 |
| B | P388 | 4 | 8 | 12.0 | 9.4 | 128 |
|   |   | 3.25 | 6 | 11.4 | 8.4 | 136 |
|   |   | 2 | 8 | 12.2 | 9.4 | 130 |
|   |   | 1 | 8 | 10.6 | 9.4 | 113 |
|   |   | 0.65 | 8 | 10.0 | 8.0 | 125 |
|   |   | 0.5 | 8 | 9.4 | 9.4 | 100 |
| B | LLC | 4 | 9 | 12.6 | 9.8 | 129 |
|   |   | 2 | 9 | 12.2 | 9.8 | 124 |
|   |   | 1 | 9 | 11.2 | 9.8 | 114 |
|   |   | 0.5 | 9 | 10.4 | 9.8 | 106 |
| B | B16 | 8 | 8 | 12.0 | 19.0 | 63 (toxic) |
|   |   | 4 | 8 | 19.8 | 19.0 | 104 |
|   |   | 2 | 8 | 19.4 | 19.0 | 102 |

[a]T/C = survival time of treated/survival time for control

The scytophycins are also useful as antifungal agents. Thus, in one aspect, this invention relates to a method of protecting plants from phytopathogenic fungi which comprises contacting the loci of the fungi with a fungicidally-effective amount of a scytophycin compound. The loci of the fungi can be a portion of the plant, such as leaves, stems, flowers or roots, or the soil wherein the fungi may be located.

Application rates will vary according to a number of factors, such as the location of the plants being protected and the severity of the fungal infection. Thus, for use in a greenhouse, the fungicidal compound is applied as a soil drench using a composition having a concentration in the range of from about 1 to about 200 ppm of active ingredient, preferably from about 5 to about 100 ppm. As is understood by those in the art, application rates used in the field are usually greater than those used in a greenhouse, and range from about 25 to about 1000 ppm.

In another embodiment, this invention relates to compositions suitable for inhibiting plant-pathogenic fungi comprising 1) a scytophycin compound in an amount effective to inhibit the growth of a plant-pathogenic fungus and 2) a suitable carrier.

The compositions for use in this embodiment desirably contain, in addition to the scytophycin compound, one or more of a number of suitable formulating carriers, including water, polyhydroxy compounds, petroleum distillates, and other dispersion media, surface-active dispersing agents, emulsifiers, and finely-divided inert solids. The concentration of scytophycin compound in these compositions will vary, depending on whether the composition is intended for direct application to plants or is intended to be subsequently diluted with an additional inert carrier or carriers, such as water, to produce the ultimate treating composition.

Treating compositions are most conveniently formulated by preparing liquid or solid concentrates, which are subsequently diluted to the desired level for use. Emulsifiable liquid concentrates can be prepared by incorporating from about 1 to about 10 percent by weight of the active ingredient and an emulsifiable agent in a suitable water-immiscible organic liquid. Such concentrates may be further diluted with water to form spray mixtures in the form of oil-in-water emulsions. Such spray compositions then comprise active compound, water-immiscible solvent, emulsifying agent, and water. Suitable emulsifying agents can be of the nonionic or ionic types, or blends thereof, and include condensation products of alkylene oxides with phenols and organic acids, polyoxyethylene derivatives of sorbitan esters, complex ether alcohols, ionics of the arylalkyl sulfonate type, and the like. Suitable water-immiscible organic liquids include aromatic hydrocarbons, aliphatic hydrocarbons, cycloaliphatic hydrocarbons, and mixtures thereof such as petroleum distillates.

Solid concentrate mixtures can be prepared by incorporating from about 10 to about 50% by weight of active compound in a finely-divided solid carrier such as bentonite, Fuller's earth, diatomaceous earth, hydrated silica, diatomaceous silica, expanded mica, talc, chalk, and the like. Such concentrates can be formulated, if desired, for direct use as dusting compositions, or can be diluted, if desired, with additional inert solid carriers to produce dusting powders containing around 0.05 to 1% by weight of a scytophycin compound. Alternatively, the surfactants, that is, dispersing and/or wetting agents, can be incorporated along with the scytophycin compound in the solid carrier to form wettable powder concentrates ranging from about 10 to about 25% by weight concentration, which subsequently can be dispersed in water or other hydroxylated carrier to form spray compositions. Suitable surfactants include condensed aryl sulfonic acids and sodium salts thereof, sodium lignosulfate, sulfonate-oxide condensate blends, alkylaryl polyether alcohols, sulfonate-/nonionic blends, anionic wetting agents, and the like.

Further, the scytophycin compound can be incorporated in solutions, simple dispersions, aerosol formulations, and other media acceptable for treating vegetation or for applying to the soil.

The antifungal compositions of this embodiment are applied to infected or susceptible plant or soil surfaces in any convenient fashion, such as by spraying, dusting, dipping, or drenching. A spray method is considered preferable, especially when large numbers of plants are involved, because such a treatment is faster and more uniform. In spraying it is usually sufficient for the infected or susceptible surfaces to be made thoroughly wet with the liquid dispersion. Good results can be obtained by using spray compositions whether they are emulsions or aqueous dispersions of solid concentrates.

Where the fungi to be controlled are in the soil, the antifungal compound can be applied to the soil directly, or it can be diluted with various inert solid or liquid diluents and then applied to the soil. In one method of application the soil surface is sprayed with a liquid dispersion or emulsion of the active ingredient. The application is allowed to remain as a coating on the surface of the soil or, alternatively, is incorporated into the soil by disking, hoeing, or other methods known to those in the art. Another method of application is to apply the active ingredient in the form of a liquid dispersion or emulsion to the soil as a drench. Thus, for the control of soil-inhabiting fungi in the greenhouse, the application rate varies from about 5 to about 200 ppm active ingredient.

Scytophycin compounds can also be used as a seed soak for seeds prior to planting. A suitable seed-soak formulation contains a scytophycin compound together with excipients such as a mixture of ethanolacetone, polyoxyethylene sorbitan monolaurate, and the like.

When used as a seed soak, control can be accomplished at an application rate of from about 50 to about 400 ppm of scytophycin compound. The seeds are allowed to soak in the formulation for about 4 hours and then are removed and planted.

The activity of scytophycin compounds against pathogenic fungi in standard in vitro agar-diffusion tests, using ¼ discs holding ~30 μL of test solution, is illustrated in Tables 6–12.

TABLE 6
In Vitro Agar Diffusion Activity of Scytophycins A and B vs. *Pythium ultimum* X751

| Compound | Level | Zone of Inhibition Size |
|---|---|---|
| Scytophycin A | 1 mg/mL | 37 mm |
| Scytophycin B | 1 mg/mL | 37 mm |

TABLE 7
In Vitro Agar Diffusion Activity of Scytophycins A and B vs. *Fungal Pathogens*

| | | Size of Zone of Inhibition (mm) | | |
|---|---|---|---|---|
| Compound | Concentration mg/mL | *Saccharomyces pastorianus* X52 | *Neurospora crassa* X846 | *Candida albicans* X657 |
| Scytophycin A | 1 | 24 | 30 | 23 |
| | 0.1 | 17 | 25 | 19 |
| | 0.01 | T$^a$ | 18 | 12 |
| Scytophycin B | 1 | 27 | 32 | 26 |
| | 0.1 | 20 | 27 | 22 |
| | 0.01 | 20 | 30 | 21 |

$^a$T = trace

TABLE 8
In Vitro Agar Diffusion Activity of Scytophycins B, D, and E vs. *Fungal Pathogens*

| | | Size of Zone of Inhibition (mm) | | |
|---|---|---|---|---|
| Compound | Concentration mg/mL | *Saccharomyces pastorianus* X52 | *Neurospora crassa* X846 | *Candida albicans* X657 |
| Scytophycin B | 1 | 24 | 36 | 31 |
| | 0.33 | 24 | 36 | 25 |
| Scytophycin D | 1 | 12 | 25 | 19 |
| | 0.33 | T$^a$ | 20 | 14 |
| Scytophycin E | 1 | 23 | 36 | 21 |
| | 0.33 | 18 | 26 | 22 |

$^a$T = trace

TABLE 9
In Vitro Agar Diffusion Activity of Scytophycin C and the Scytophycin B Derivatives vs. *Fungal Pathogens*

| | | Size of Zone of Inhibition (mm) | | |
|---|---|---|---|---|
| Compound | Concentration mg/mL | *Saccharomyces pastorianus* X52 | *Neurospora crassa* X846 | *Candida albicans* X657 |
| Scytophycin C | 1 | 17 | 30 | 22 |
| Compound 7 | 1 | 19 | 28 | 20 |
| Compound 8 | 1 | —$^a$ | 13 | — |

$^a$— = not active

TABLE 10
In Vitro Agar Diffusion Activity of Scytophycins A and B compared with Majusculamide C vs. *Fungal Pathogens*

| | | Size of Zone of Inhibition (mm) | | |
|---|---|---|---|---|
| Compound | Conc. mg/mL | *Pythium ultimum* X751 | *Rhizoctonia solani* X767 | *Sclerotina homoeocarpa* X768 |
| Scytophycin A | 1.0 | >30 | 30 | >30 |

TABLE 10-continued

In Vitro Agar Diffusion Activity of Scytophycins A and B compared with Majusculamide C vs. *Fungal Pathogens*

| Compound | Conc. mg/mL | Size of Zone of Inhibition (mm) | | |
|---|---|---|---|---|
| | | *Pythium ultimum* X751 | *Rhizoctonia solani* X767 | *Sclerotina homoeocarpa* X768 |
| | 0.1 | >30 | 23 | 30 |
| | 0.01 | 20 | 13 | 20 |
| Scytophycin B | 1.0 | 30[a] | >30 | >30 |
| | 0.1 | 30[a] | >30 | >30 |
| | 0.01 | 30 | 30 | >30 |
| Majusculamide C | 1.0 | >30 | 20[a] | 17 |
| | 0.1 | 18 | — | — |
| | 0.01 | 10[a] | — | — |

[a]Overgrowth

TABLE 11

In Vitro Agar Diffusion Activity of Scytophycins B, D and E vs. *Fungal Pathogens*

| Compound | Conc. mg/mL | Size of Zone of Inhibition (mm) | | |
|---|---|---|---|---|
| | | *Pythium ultimum* X751 | *Rhizoctonia solani* X767 | *Sclerotina homoeocarpa* X768 |
| Scytophycin B | 1.0 | 30 | 46[a] | 44 |
| | 0.33 | 30 | 40 | 40 |
| Scytophycin D | 1.0 | 27 | 30 | 26 |
| | 0.33 | 24 | 22 | 20 |
| Scytophycin E | 1.0 | 40 | 46[a],25 | 35 |
| | 0.33 | 30 | 33[a],15 | 33 |

[a]Overgrowth

TABLE 12

In Vitro Agar Diffusion Activity of Scytophycins C and the Scytophycin B Derivatives vs. *Fungal Pathogens*

| Compound | Conc. mg/mL | Size of Zone of Inhibition (mm) | | |
|---|---|---|---|---|
| | | *Pythium ultimum* X751 | *Rhizoctonia solani* X767 | *Sclerotina homoeocarpa* X768 |
| Scytophycin C | 0.5 | 12[a] | 30 | 32 |
| Compound 7 | 1.0 | 12 | 32 | 32 |
| Compound 8 | 1.0 | —[b] | 15[a] | 12 |

[a]Overgrowth
[b]— = not active

The following examples are provided to illustrate this invention.

EXAMPLE 1

Production of Scytophycins A, B, C, D and E

Unialgal, non-axenic cultures of *Scytonema pseudohofmanni* ATCC 53141 were grown in 25-L glass bottles containing an aqueous inorganic medium having the following composition:

| Ingredient | Amount |
|---|---|
| $NaNO_3$ | 200 mg/L |
| $NH_4Cl$ | 10 mg/L |
| $K_2HPO_4.3H_2O$ | 65 mg/L |
| $MgSO_4.7H_2O$ | 50 mg/L |
| $CaCl_2.2H_2O$ | 13 mg/L |
| 3-(N-morpholino)-propanesulfonic acid | 627 mg/L |
| Minor elements solution[a] | 1 mL/L |
| Trace elements solution[b] | 3/25 (0.12) mL/L |

Prior to autoclaving, the pH of the complete medium is adjusted to 7 with sodium hydroxide.

| [a]Minor Elements Solution: | |
|---|---|
| Ingredient | Amount |
| $FeCl_3.6H_2O$ | 0.54 g/L |
| $Na_2EDTA$ | 3.0 g/L |
| $H_3BO_3$ | 0.62 g/L |
| $MnCl_2.4H_2O$ | 1.4 g/L |
| $ZnCl_2$ | 0.10 g/L |
| $CoCl_2.6H_2O$ | 5 mg/L |
| $CuCl_2.2H_2O$ | 34 mcg/L |

| [b]Trace Elements Solution: | |
|---|---|
| Ingredient | Amount (mg/10 L of 0.1 N $H_2SO_4$) |
| $MoO_3$ (85%) | 176.4 |
| $NH_4VO_3$ | 229.6 |
| $Cr_2K_2(SO_4)_4.24H_2O$ | 960.2 |
| $NiSO_4.6H_2O$ | 447.8 |
| $Co(NO_3)_2.6H_2O$ | 493.8 |
| $Na_2WO_4.sH_2O$ | 179.4 |
| $Al_2(SO_4)3$ | 317.1 |
| $As_2O_3$ | 66.1 |
| $CdCl_2$ | 81.5 |
| $SrSO_4$ | 104.9 |
| $HgCl_2$ | 67.7 |
| $PbCl_2$ | 67.1 |
| $LiCl$ | 305.5 |
| $Rb_2SO_4$ | 78.1 |
| $NaBr$ | 64.4 |
| $KI$ | 65.4 |
| $NaF$ | 110.5 |
| $Na_2SeO_4$ | 119.4 |

-continued

| | |
|---|---|
| Be(NO$_3$)$_2$.3H$_2$O | 1037.0 |

The cultures were illuminated continuously at an incident intensity of 330 microEinsteins m$^{-2}$sec$^{-1}$ from banks of cool-white fluorescent tubes and were vigorously aerated with 0.5% carbon dioxide in air. Following incubation at 24±1° C. for periods ranging from 25 to 33 days, the alga was harvested by filtration or centrifugation at 5000 x g in a refrigerated continuous flow centrifuge and then were freeze dried. Yields of the lyophilized algal cells were typically 0.3 to 0.4 g per liter of culture.

EXAMPLE 2

Isolation of Scytophycins A and B

Dried algal cells (23 g); produced as described in Example 1, were homogenized in a Waring blender with one liter of ethanol-water (2:3) for ten minutes. The mixture was shaken overnight and then centrifuged at 12,000 x g for twenty minutes. The supernate was concentrated under reduced pressure at 40° C. to a volume of 300 mL, and 100 mL of 95% ethanol was added to give 400 mL of an ethanol-water (1:3) solution which was then subjected to sonication for two minutes to disperse a fine floc.

This solution was passed through a 1-mL C-18 column (Sep-pak, Millipore Corporation) in 10-mL portions at a flow rate of 5-10 mL/min. After the passage of each 10-mL aliquot, the C-18 column was washed with 10 mL of ethanol-water (1:3). The crude scytophycins were eluted from the column with 15 mL of 50% ethanol-water. The column was then regenerated for the next run by a reversed wash with 95% ethanol (to remove accumulated precipitate) followed by a normal wash with 5 mL of water. The combined 50% ethanol-water effluent (600 mL) was concentrated in vacuo to remove the ethanol, and the aqueous concentrate (300 mL) was lyophilized.

The residual semisolid was dissolved in ethanol-water (7:3) and filtered; the filtered solution (4.25 mL) was subjected to reverse-phase HPLC in 200-μL portions on a Beckman 1-cm×25-cm column of ODS bonded to 5-μm spherical silica-based packing, using 65% acetonitrile and 35% 0.10 M triethylamine and 0.122 M acetic acid in water as the eluant. Using a flow rate of 4 mL/min, a 200-μL aliquot could be introduced onto the column every 10 minutes. Elution was monitored by ultraviolet absorption at 300 nm. Two fractions having retention times of 6'20" (A) and 7'50" (B) were collected. Fractions A and B showed single peaks at 9'20" and 12'46" when each one was rechromatographed on the same column, using 57.5% CH$_3$CN–42.5% Et$_3$N-/HOAc buffer. Water (40 mL) was added to each fraction, and the acetonitrile was evaporated under reduced pressure. The turbid aqueous mixture was then lyophilized twice to remove the volatile buffer. Fraction A provided 14.3 mg of scytophycin A (0.062%), and fraction B yielded 34 mg of scytophycin B (0.15%).

EXAMPLE 3

Isolation of Scytophycins A, B, C, D and E

Freeze-dried algal cells (176 g), prepared as described in Example 1, were steeped in 6 L of dichloromethane/isopropanol (1:1) for 24 hours at room temperature with stirring. The mixture was filtered, and the extract was evaporated to give a semi-solid residue. This material was dissolved in 90% methanol (2 L), and the particulates were separated by filtration. The filtrate was partitioned with hexane (2 L). The 90% methanol layer was adjusted in concentration to 65% methanol with water and extracted with dichloromethane (2×2 L). The CH$_2$Cl$_2$ layer was evaporated to give a residue which was subjected to gel filtration on LH-20 Sephadex (83×9 cm) using hexane/dichloromethane (1:4) as the eluant.

The fractions eluting from 2100 mL to 2600 mL contained mostly scytophycins B and C, whereas the fractions eluting from 2600 mL to 3100 mL contained mostly scytophycin A with small amounts of scytophycins D and E. Each set of fractions was dissolved in a minimum amount of absolute ethanol and applied to a 2-cm×0.9-cm column of BondElut C-18 (Analytichem International, Harbor City, Calif.) which had been previously equilibrated with 70% ethanol; the scytophycins were separated from most of the pigments by elution with 15 mL of 70% ethanol.

Final purification of the fraction containing scytophycins B and C was achieved by reverse-phase HPCL on ODS-2 (Whatman M9 10/50 column) using either 70% acetonitrile/30% aqueous triethylammonium acetate buffer (0.1M triethylamine, 0.122M acetic acid) or 85% MeOH as the eluant. Scytophycin B (161 mg) eluted prior to scytophycin C (61 mg) on this column.

The fraction containing scytophycins A, D and E was further purified by normal phase HPLC on silica using methanol/dichloromethane (3:97) as the eluant. After a small amount of scytophycin B was eluted, scytophycins D (6 mg), E (6 mg) and A (90 mg) were obtained.

EXAMPLE 4

7-O-Acetyl-scytophycin B

Scytophycin B was reacted with 1.2 equivalents of acetic anhydride, 1.2 equivalents of triethylamine, and a catalytic amount of 4-dimethylaminopyridine in methylene chloride at 25° C. for 5 hours to give 7-O-acetyl-scytophycin B.

EXAMPLE 5

Aldehyde 7 from Scytophycin B

Scytophycin B (18 mg) was dissolved in acetic acid (18 mL) and ethanol (18 mL). After being stirred at room temperature for 1 day, the reaction mixture was evaporated under reduced pressure. The residue was then passed through a Bond Elut column of C$_{18}$, eluting with 30 mL of ethanol:water (7:3) to give compound 7: UV λmax (MeOH): 264.5 nm (ε 20,000); MS (FAB): m/z 783 (M+Na)$^+$, 761 (M+H) and 729 (M—CH$_3$OH+H)$^{30}$.

EXAMPLE 6

Primary Alcohol 8 from Scytophycin B

Aldehyde 7, obtained as described in Example 5, was dissolved in ethanol (10 mL) and cooled at 0° C. To this solution, sodium borohydride (1 mg, 1.1 equiv) in ethanol (0.5 mL) was added. The mixture was stirred at 0° C. for 30 minutes. After addition of acetone (2 mL), the reaction mixture was evaporated to a small volume (ca. 1 mL). Then brine and ethyl acetate were added. This solution was extracted with ethyl acetate to give compound 8: UV λmax (MeOH): 263 nm (ε 16,000); MS (FAB): m/z 785 (M+Na)+ and 763 (M+H)+.

EXAMPLE 7

Di-p-Bromobenzoate of Compound 8

Compound 8, obtained as described in Example 6, and a catalytic amount of 4-dimethylaminopyridine were dissolved in dichloromethane (6 mL). To this solution, triethylamine (50 μL) and then p-bromobenzoyl chloride (30 mg) were added. After being stirred at room temperature for 1 day, the reaction mixture was poured onto a silica-gel column (0.8×7 cm) packed with dichloromethane. Elution with dichloromethane (20 mL) gave unreacted acid chloride; then elution with dichloromethane/ethyl acetate (2:1) afforded crude product.

This product was further purified by silicagel chromatography (0.8×7-cm column), eluting with hexane/ethyl acetate (4:1) to give 9 mg of the di-p-bromobenzoate of compound 8: mp: 105°–106° C. (MeOH—CH$_2$Cl$_2$); $^1$H NMR (acetone-d$_6$): δ7.98 (m 4H, aromatic Hs), 7.74 (m 4H, aromatic Hs), 7.49 (d, H-3), 6.01 (m, H-5), 5.85 (m, H-11), 5.78 (d, H-2), 5.68 (br d, H-10), 5.36 (br t, H-7), 5.25 (d, H-21), 4.31 (br d, H-9), 4.54 (dd, H-32), 4.27 (dd, H′-32), 3.82 (dd, H-15), 3.75 (dd, H-17), 3.42 (s, MeO), 3.31 (s, MeO), 3.29 (s, MeO), 3.23 (s, MeO), 2.70 and 2.60 (each d, CH$_2$-16), 1.88 (br s, Me-4), 1.12 (d, sec-Me), 1.09 (d, sec-Me), 0.92 (d, sec-Me), 0.89 (d, sec-Me), and 0.79 (d, sec-Me).

EXAMPLE 8

Diacetate of Compound 8

Compound 8 (21 mg) was acetylated with acetic anhydride (0.5 mL) and pyridine (2 mL) at room temperature for 1 day. After addition of methanol (3 mL), the reaction mixture was evaporated and purified by silica-gel column chromatography, eluting with hexane/ethyl acetate (2:1) to give 10 mg of the diacetate of compound 8: $^1$H NMR (acetone-d$_6$): δ 7.45 (d, H-3), 5.92 (m, H-5), 5.83 (m, H-11), 5.76 (d, H-2), 5.64 (br d, H-10), 5.23 (d, H-21), 5.08 (t, H-7), 4.23 (d, H-9), 4.20 (dd, H-32), 3.98 (dd, H-32), 3.79 (dd, H-15), 3.73 (dd, H-17), 3.38 (s, MeO), 3.27 (s, MeO), 3.24 (s, MeO), 3.20 (s, MeO), 2.67 and 2.57 (each d, CH$_2$O), 1.85 (br d, Me-4), 1.07 (d, sec-Me), 1.07 (d, sec-Me), 0.89 (d, sec-Me), 0.89 (d, sec-Me) and 0.82 (d, sec-Me).

EXAMPLE 9

7-O-(p-Bromobenzoyl)scytophycin C

Scytophycin C (15 mg) and 4-dimethylaminopyridine (a catalytic amount) were dissolved in dichloromethane (3 mL). To this solution, triethylamine (100 μL) and then p-bromobenzoyl chloride (50 mg) were added. After being stirred at room temperature for 8 hours, the mixture was poured onto a silica-gel column (0.7×8 cm). Elution with dichloromethane (20 mL) gave unreacted acid chloride; then elution with ethyl acetate/dichloromethane (1:1) afforded crude products. Purification by reverse-phase HPLC (Whatman ODS 2), eluting with MeOH/H$_2$O (94:6), afforded 7-O-(p-bromobenzoyl)scytophycin C: UV λmax (MeOH): 252.5 nm (ε 31,600); $^1$H NMR (acetone-d$_6$) δ 8.35 (s, H-34), 8.11 (s, H-34 of the minor conformer), 7.98 (d, aromatic Hs), 7.74 (d, aromatic Hs), 7.67 (d, H-3), 6.78 (d, H-32), 7.10 (d, H-32 of the minor conformer), 6.18 (t, H-5), 5.83 (d, H-2), 5.82 (m, H-11), 5.75 (d, H-10), 5.45 (m, H-7), 5.18 (d, H-21), 5.11 (dd, H-31), 4.35 (d, H-9), 4.14 (d, OH-23), 3.71 (br d, H-15), 3.54 (t, H-17), 3.35 (s, MeO), 3.34 (s, MeO), 3.31 (s, MeO), 3.21 (s, MeO), 3.00 (s, Me-N33), 3.12 (s, Me-N33 of the minor conformer), 1.89 (br s, Me-4), 1.16 (d, sec-Me), 0.99 (d, sec-Me), 0.95 (d, sec-Me), 0.94 (d, sec-Me), 0.88 (d, sec-Me) and 0.86 (d, sec-Me).

EXAMPLE 10

Scytophycin B Antifungal Composition

An antifungal composition containing scytophycin B can be prepared as follows:

Dissolve scytophycin B (10 mg) in 1 mL of acetone:ethanol (1:1) to which 5 to 10% of a surfactant such as Tween 20 has been added. Add water (99 mL) to result in a final concentration of 100 ppm of scytophycin B, 1% solvent and 0.05 to 0.1% surfactant.

This antifungal solution can be sprayed on plants or soil to inhibit fungal pathogens.

We claim:

1. A compound of the formula wherein R$^3$ represents —CHO or —CH$_2$OH, or a C$_1$–C$_6$-alkanoyl or benzoyl or halo-, hydroxyl- or C$_1$–C$_3$-alkoxy-substituted C$_1$–C$_6$-alkanoyl or benzoyl ester derivative thereof.

2. A compound of claim 1 wherein R$^3$=—CHO.

3. A compound of claim 1 wherein R$^3$=—CH$_2$OH.

4. A composition suitable for inhibiting susceptible fungi comprising the (1) an effective amount of a compound selected from the aldehyde or alcohol derivative of scytophycin B or a C$_1$–C$_6$-alkanoyl or benzoyl ester or halo-, hydroxy- or C$_1$–C$_3$-alkoxy substituted-C$_1$–C$_6$-alkanoyl or benzoyl esters thereof; and (2) a suitable carrier.

5. A method for inhibiting susceptible fungi which comprises contacting the locus of the fungus with an effective amount of a composition of claim 4.

* * * * *

UNITED STATES PATENT AND TRADEMARK OFFICE
CERTIFICATE OF CORRECTION

PATENT NO. : 4,996,229
DATED : February 26, 1991
INVENTOR(S) : Moore, et al

It is certified that error appears in the above-indentified patent and that said Letters Patent is hereby corrected as shown below:

On the title page, Item [75]: Inventors should read as follows:
--Richard E. Moore;and Gregory M.L. Patterson, both of Honolulu, Hi.; and Jon S. Mynderse, Indianapolis, Ind.--

Column 22, Claim 4, line 51, "comprising the (1)" should read --comprising (1)--. at line 55, "esters" should read --ester--.

Signed and Sealed this

Second Day of November, 1993

*Attest:*

BRUCE LEHMAN

*Attesting Officer*   *Commissioner of Patents and Trademarks*